(12) United States Patent
Hubbard, Jr. et al.

(10) Patent No.: US 8,342,836 B2
(45) Date of Patent: Jan. 1, 2013

(54) FLEXIBLE CARRIER MOLD

(75) Inventors: Wade Monroe Hubbard, Jr., Liberty Township, OH (US); Kevin Charles Strong, Loveland, OH (US); Michael John Mers-Kelly, Hartford, ME (US); Daniel Raymond Wiegele, Cincinnati, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 25 days.

(21) Appl. No.: 12/776,578

(22) Filed: May 10, 2010

(65) Prior Publication Data

US 2010/0221378 A1 Sep. 2, 2010

Related U.S. Application Data

(63) Continuation of application No. 12/259,581, filed on Oct. 28, 2008, now Pat. No. 7,740,787.

(51) Int. Cl.
*B29C 45/40* (2006.01)
*B29C 45/44* (2006.01)

(52) U.S. Cl. . 425/392; 425/395; 425/440; 425/DIG. 14; 28/119

(58) Field of Classification Search ............... 425/392, 425/395, 440, DIG. 5, DIG. 14, DIG. 58; 28/118, 119
See application file for complete search history.

(56) References Cited

U.S. PATENT DOCUMENTS

| | | | | |
|---|---|---|---|---|
| 2,425,004 A | * | 8/1947 | Rabell | 28/118 |
| 4,479,791 A | * | 10/1984 | Sprague | 604/14 |
| 5,153,971 A | | 10/1992 | Van Iten | |
| 5,630,977 A | * | 5/1997 | Catalanotti et al. | 264/318 |
| 5,709,652 A | * | 1/1998 | Hagerty | 604/15 |
| 6,056,714 A | * | 5/2000 | McNelis et al. | 604/14 |
| 6,419,777 B1 | * | 7/2002 | Achter et al. | 156/217 |
| 6,923,789 B2 | * | 8/2005 | LeMay et al. | 604/110 |
| 7,047,608 B2 | | 5/2006 | Sageser et al. | |
| 7,059,026 B2 | | 6/2006 | Friese et al. | |
| 2004/0064082 A1 | * | 4/2004 | LeMay et al. | 604/11 |
| 2005/0022349 A1 | | 2/2005 | Pham et al. | |
| 2005/0027275 A1 | | 2/2005 | Wasson et al. | |
| 2007/0234532 A1 | | 10/2007 | Gilbert et al. | |
| 2008/0065041 A1 | | 3/2008 | Stan et al. | |

* cited by examiner

*Primary Examiner* — Richard Crispino
*Assistant Examiner* — Robert Dye
(74) *Attorney, Agent, or Firm* — Andres E. Velarde; Megan C. Hymore

(57) ABSTRACT

A carrier mold having prongs that produces shaped tampons is provided. When subjected to pressure the prongs of the carrier mold flex to completely or substantially close one end of the carrier mold. A method of forming a shaped tampon using the carrier mold is also provided.

20 Claims, 13 Drawing Sheets

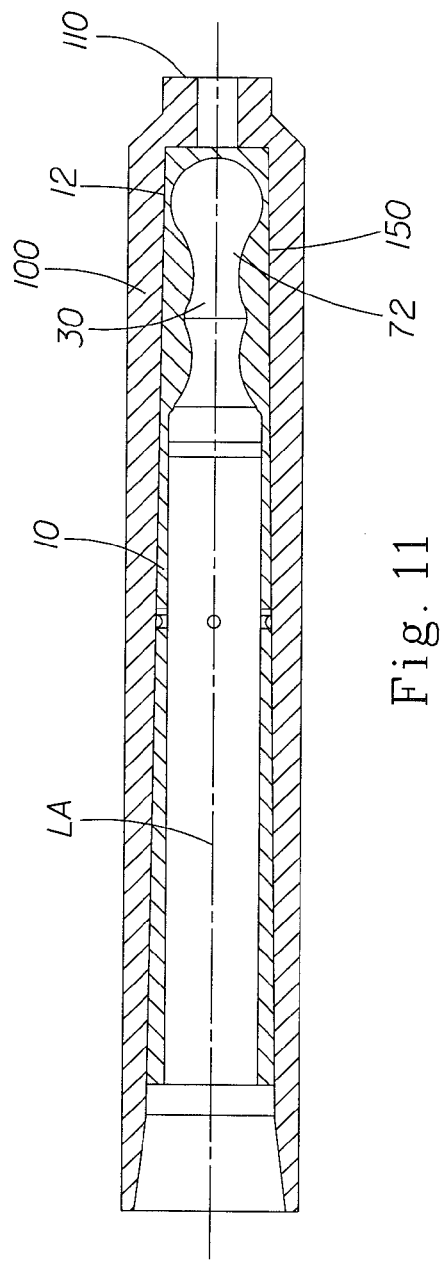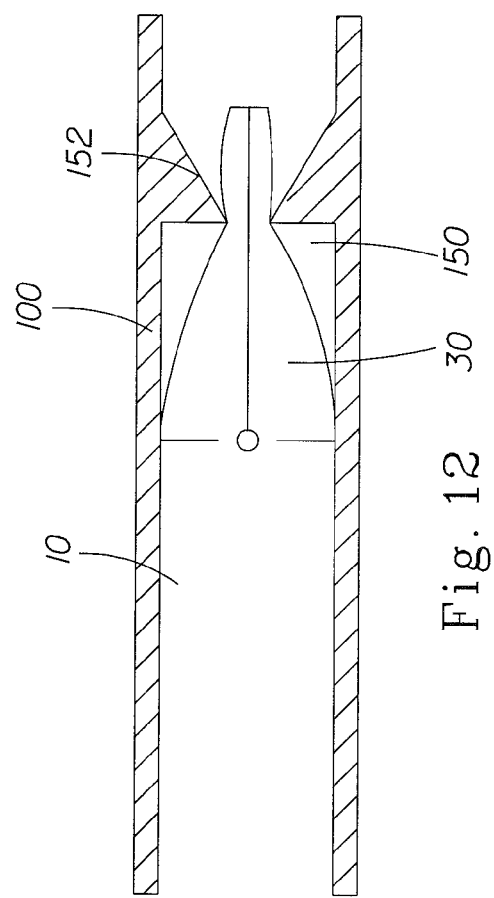
Fig. 11
Fig. 12

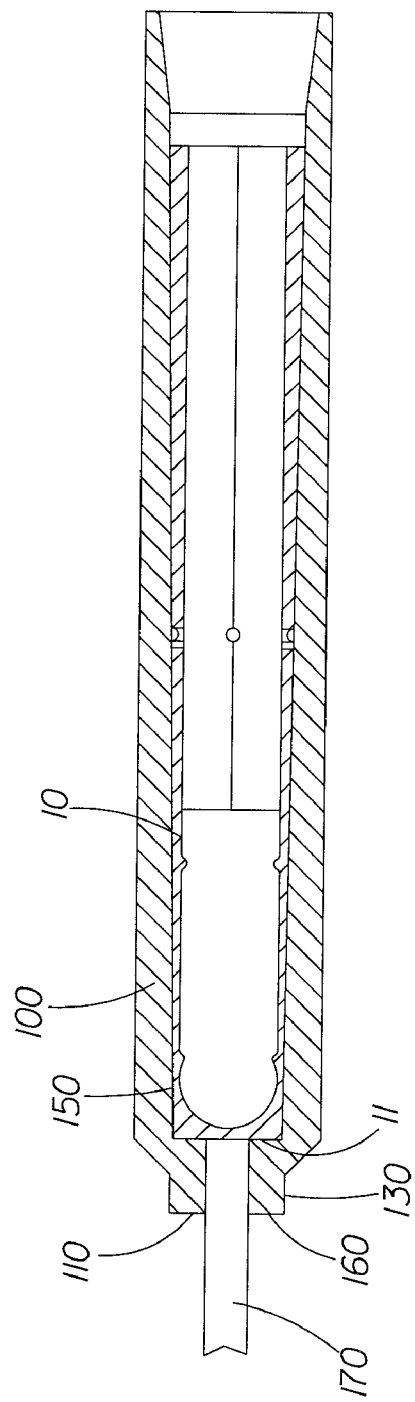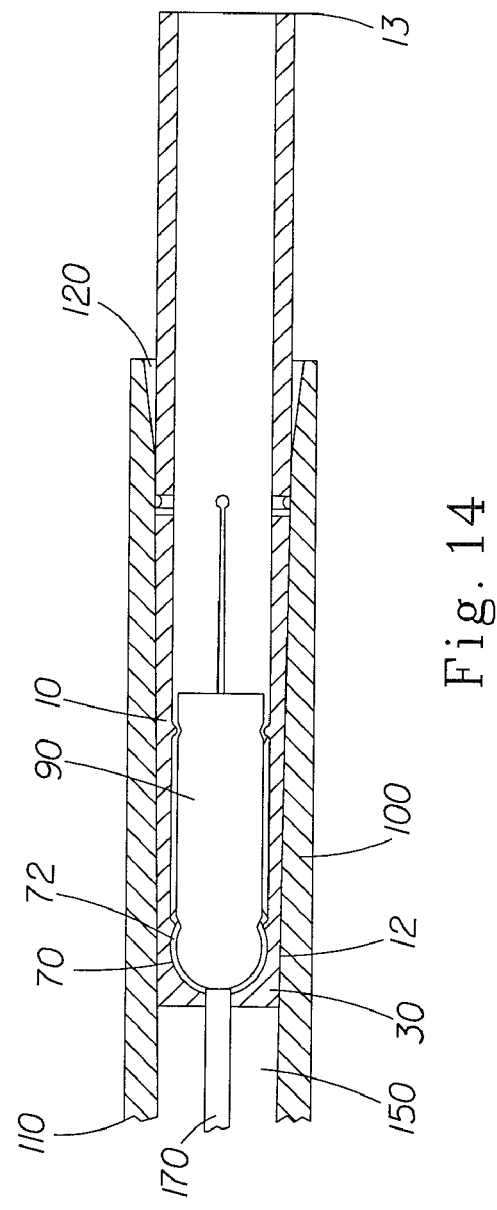

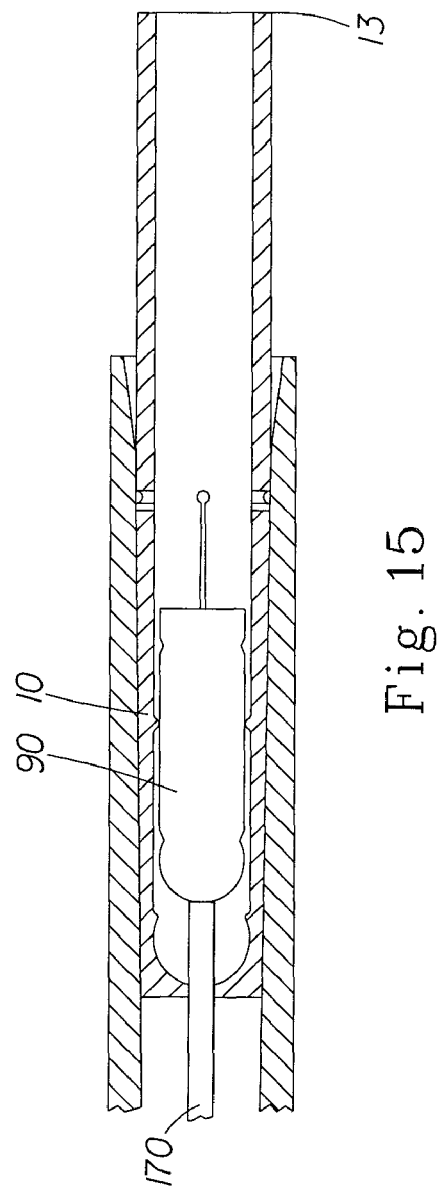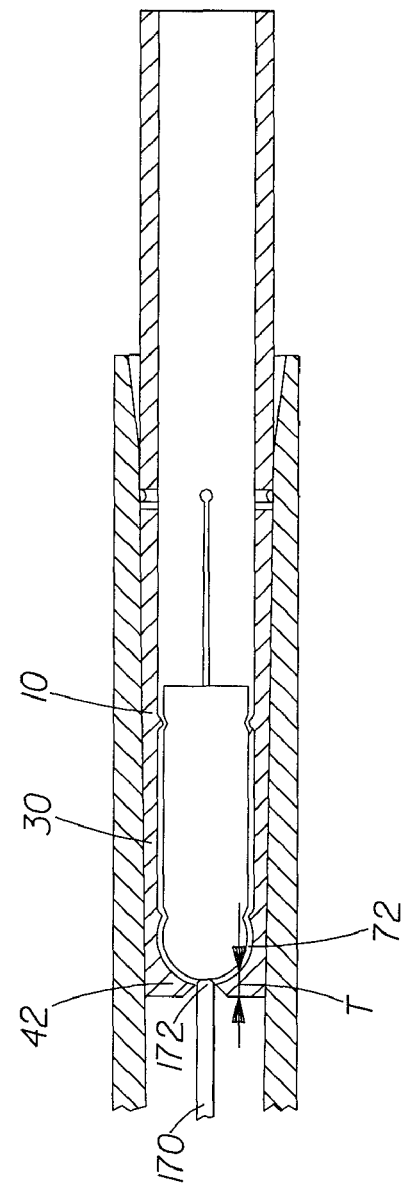

FLEXIBLE CARRIER MOLD

CROSS REFERENCE TO RELATED APPLICATION

This application is a continuation of U.S. application Ser. No. 12/259,581 filed Oct. 28, 2008 now U.S. Pat. No. 7,740,787.

FIELD OF THE INVENTION

The invention relates to a carrier mold and a method of using a carrier mold to produce a shaped tampon.

BACKGROUND OF THE INVENTION

Tampons are well known as absorbent articles, and specifically as feminine hygiene articles effective in the absorption of menses inside the vagina. Tampons are generally cylindrical, compressed batts of absorbent fibers that expand upon being wetted in use. For example, once inserted inside the vagina, tampons tend to expand as fluid is absorbed, thereby increasing in volume to fill more of the space within the vagina. As the tampon expands, more surface area is exposed that can contact the walls of the vagina, thereby intercepting more fluid and preventing fluid escape and leakage.

Tampons typically have a cylindrical "bullet" like appearance that is often perceived by consumers as lacking an aesthetically pleasing appearance. Further, cylindrical tampons have a perimeter that is substantially the same along the length of the tampon. Tampons having a substantially constant perimeter along their length do not reflect the contours of the vaginal cavity, which varies in its width as measured from the vaginal opening to the cervix. These differences in shape between the vaginal cavity and that of cylindrical tampons reduces the effectiveness of the cylindrical tampons, in that the wider areas of the vaginal cavity will not be contacted by the cylindrical tampon, which is needed for absorption, and consequently menses will by pass the cylindrical tampon to eventually pass through the vaginal opening.

An answer to the limitations of cylindrically-shaped tampons has been the development of shaped tampons. In comparison to cylindrical tampons, shaped tampons generally have differing perimeters along their length, such that some shaped tampons have an "hourglass" or "bottle shaped" appearance. Consumers have a pleasing opinion of the shape, as it possesses a more natural and comfortable appearance than the rigid and symmetrical form of cylindrical tampons. In comparison to cylindrical shaped tampons, shaped tampons also have the capability to provide a consumer with increased performance, as the parts of the shaped tampon most likely to encounter menses, the end closest the cervix and the end closest the vaginal opening can have greater perimeters than the central portion of the shaped tampon. This allows a shaped tampon to provide increased protection upon insertion, without the need for fluid uptake to drive expansion.

The production of shaped tampons has been problematic, as a shaped tampon cannot be laterally ejected from the unitary molds used to produce cylindrical tampons, due to a shaped tampon having varying perimeters along its length. When the sections of a shaped tampon having larger perimeters encounter the portions of the unitary mold used to form the narrower perimeters of the shaped tampon, the larger sections will provide resistance to the lateral movement used for evacuating the shaped tampon. This resistance caused by the larger sections of the shaped tampon results in damage to the tampon and the mold.

In an attempt to solve the evacuation problem, processes used for the production of cylindrical tampons have been modified. The modifications have usually taken the form of adding an additional step following compression of the pledget. This additional step has involved transferring the compressed pledget into a two-part "clam-shell" mold. A clam-shell mold is composed of two complementary halves that are brought together to form a complete mold for the formation of shaped tampons. The clam-shell mold has been favored, as a compressed pledget can be laterally transferred to the mold and shaped. However, to remove the shaped tampon the clam-shell mold must be opened and the shaped tampon manually removed. This extra production step decreases the efficiency of the method and increases the cost, making the production of shaped tampons, currently, cost-prohibitive.

Accordingly, there is a need for a mold that can replace clam-shell molds, and which can work with current cylindrical tampon production methods.

Further, there is a need for a method of producing a shaped tampon that does not include a step that burdens the process by imposing labor intensive conditions that reduce production efficiency and increase cost.

SUMMARY OF THE INVENTION

A carrier mold is provided which comprises an outer surface, an inner surface, a first end, a second end opposite the first end, a body, and at least two prongs, each prong having a proximal base and a distal end. Wherein the at least two prongs are separated by a discrete space, and the inner surface defines an inner cavity for producing shaped tampons.

A secondary sleeve and carrier mold combination is provided. The secondary sleeve comprises an inner surface that defines an inner space having a diameter, a pushrod end, and an evacuation end. The carrier mold is disposed within the secondary sleeve and comprises an outer surface, an inner surface, a first end, a second end opposite the first end, a body, and at least two prongs, each prong having a proximal base and a distal end. The at least two prongs are separated by a discrete space, and the inner surface defines an inner cavity for producing shaped tampons. Further, the inner space of the secondary sleeve is capable of receiving the carrier mold and providing pressure to the at least two prongs of the carrier mold.

A method of producing a shaped tampon is provided. The method comprises the steps of: (a) providing a carrier mold having an outer surface, an inner surface, a first end, a second end opposite the first end, a body, and at least two prongs, each prong having a proximal base and a distal end; wherein the at least two prongs are separated by a discrete space; and wherein the inner surface defines an inner cavity having an open proximal end and an intermittently closed distal end; (b) providing a secondary sleeve having an inner surface, a pushrod end, and an evacuation end, wherein the inner surface defines an inner space that provides pressure to the at least two prongs; (c) inserting the carrier mold into the inner space of the secondary sleeve; (d) transferring a pledget into the carrier mold inner cavity; (e) providing a pushrod; (f) contacting the pushrod with the first end of the carrier mold; and (g) moving the carrier mold using the pushrod.

In certain embodiments, the at least two prongs flex to completely or substantially close the intermittently closed distal end of the carrier mold inner cavity after the carrier mold has been inserted into the inner space of the secondary sleeve, and subsequent to the first end of the carrier mold being contacted by the pushrod the at least two prongs unflex as the carrier mold is moved to allow the pushrod to contact the shaped tampon, and evacuate the shaped tampon from the carrier mold inner cavity.

BRIEF DESCRIPTION OF THE DRAWINGS

FIG. 11 is a longitudinal cross-sectional view of a secondary sleeve and carrier mold combination of the present invention.

FIG. 12 is a longitudinal cross-sectional view of a secondary sleeve and carrier mold combination of the present invention.

FIG. 13 is a longitudinal cross-sectional view of a secondary sleeve and carrier mold combination of the present invention.

FIG. 14 is a longitudinal cross-sectional view of a secondary sleeve and carrier mold combination of the present invention.

FIG. 15 is a longitudinal cross-sectional view of a secondary sleeve and carrier mold combination of the present invention.

FIG. 16 is a longitudinal cross-sectional view of a secondary sleeve and carrier mold combination of the present invention.

DETAILED DESCRIPTION OF THE INVENTION

Figure 1:
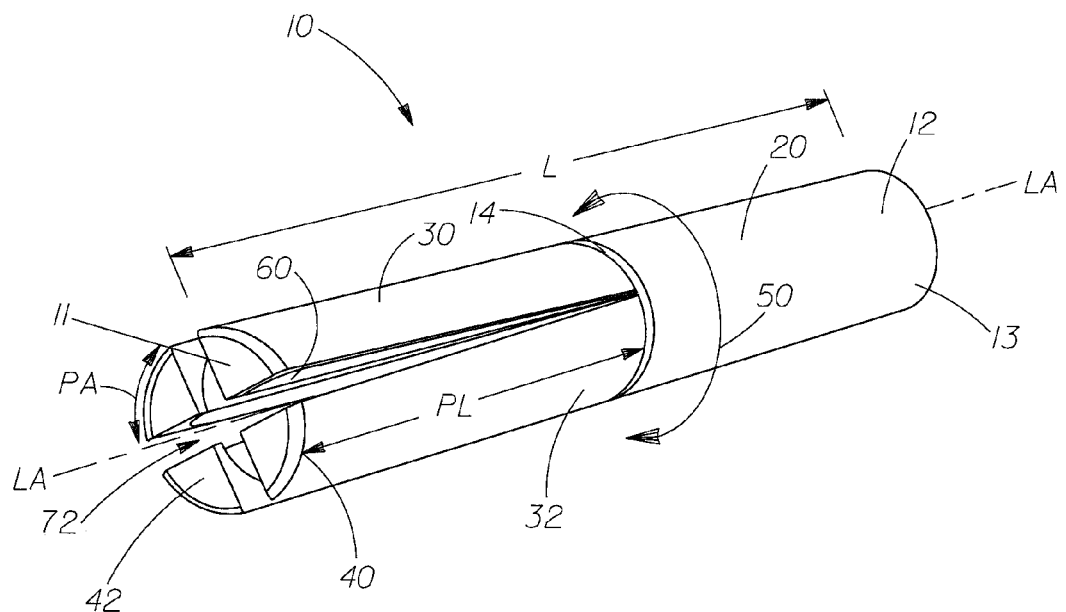
FIG. 1 is a perspective view of a carrier mold of the present invention.

The present invention is directed to a carrier mold having prongs that flex and an intermittently closed inner cavity capable of forming shaped tampons. When subjected to pressure, for example, in certain embodiments, by the carrier mold being positioned within a secondary sleeve, the prongs of a carrier mold completely or substantially close the distal end of the carrier mold's inner cavity, allowing the inner cavity to produce a shaped tampon. A method of forming a shaped tampon using a carrier mold is also disclosed, wherein the prongs of a carrier mold flex to close the distal end of the inner cavity, and a pledget that in certain embodiments is compressed is introduced to the inner cavity through the open proximal end. A shaped tampon is then formed in the inner cavity of the carrier mold and evacuated from the open proximal end of the inner cavity using a pushrod.

As used herein, the term "pledget" refers to a construction of absorbent material prior to the compression of such construction into a shaped tampon. A pledget can have a variety of shapes, including but not limited to, oval, round, chevron, square, rectangular, trapezoidal, and the like. To produce a shaped tampon, a pledget may be compressed into a generally cylindrical configuration in the radial direction, axially along the longitudinal axis or in both the radial and axial directions. While a pledget may be compressed to have a substantially circular cross-section, other cross-sections are possible. These may include cross-sections that may be described as rectangular, triangular, trapezoidal, semi-circular or other suitable cross-sections. A pledget may comprise an overwrap, skirt, secondary member, withdrawal member, or any combination thereof.

A pledget may include one or more overwraps. The overwrap can be any suitable material, such as, for example, rayon, cotton, bicomponent fibers, polyethylene, polypropylene, other suitable natural or synthetic fibers known in the art, and mixtures thereof. In certain embodiments, a pledget can comprise an overwrap material that substantially encloses the pledget. In addition, or alternatively, a pledget can include an overwrap material that extends beyond the withdrawal end and forms a finger cover or absorbent skirt.

A pledget can additionally include a withdrawal member. The withdrawal member can be any suitable configuration, such as one or more cords, strings, finger covers, ribbons, an extension of a material of the device, or combinations thereof. The withdrawal member can be made of any suitable material, such as cotton or rayon. The withdrawal member can optionally be provided with a secondary absorbent member, such as a mass of secondary absorbent material attached to the withdrawal cord proximate the withdrawal end of the pledget. Secondary absorbent members that may be used are described in, e.g., U.S. Pat. No. 6,258,075.

The term "absorbent material" as used herein can be constructed from a wide variety of materials commonly used in absorbent articles. Such materials include, but are not limited to synthetic fibers, natural fibers, or combinations thereof. The natural fibers may include, but are not limited to, cotton, wood pulp, flax, hemp, and rayon, such as GALAXY Rayon (a tri-lobed rayon structure) available as 6140 Rayon; or SARILLE L rayon (a round fiber rayon), both available from Kelheim Fibers of Kelheim, Germany, cotton, wood pulp, flax, and hemp. The synthetic fibers can include, but are not limited to, fibers such as polyester, polyolefin, nylon, polypropylene, polyethylene, polyacrylic, vinyl polyacetate, polyacrylate, cellulose acetate, or bicomponent fibers, such as bicomponent polyethylene and polypropylene fibers. Additional absorbent material includes materials such as, peat moss, absorbent foams (such as those disclosed in U.S. Pat. No. 3,994,298), capillary channel fibers (such as those disclosed in U.S. Pat. No. 5,356,405), high capacity fibers (such as those disclosed in U.S. Pat. No. 4,044,766), superabsorbent polymers or absorbent gelling materials (such as those disclosed in U.S. Pat. No. 5,830,543), may be incorporated into the shaped tampon.

As used herein, "compression" refers to the process of pressing, squeezing, compacting or otherwise manipulating the shape, length, width, or volume of a material to obtain a tampon having a vaginally insertable shape. The term "compressed" refers to the state of a material or materials subsequent to compression. Conversely, the term "uncompressed" refers to the state of a material or materials prior to compression. The term "compressible" is the ability of a material to undergo compression.

The term "attached," as used herein, encompasses configurations in which a first element is directly secured to a second element by affixing the first element directly to the second element and configurations in which the first element is indirectly secured to the second element by affixing the first element to one or more intermediate members, which in turn are affixed to the second element.

The term "contacted," as used herein, encompasses configurations in which a first element is directly contacted with a second element and configurations in which the first element is indirectly contacted with the second element by contacting the first element to one or more intermediate members, which in turn are contacted with the second element.

As used herein, "carrier mold" refers to a structure for shaping a pledget during compression or retaining the shape of a compressed pledget subsequent to compression, for example during the stabilization process. Carrier molds comprise an inner surface defining an inner cavity and an outer surface. The inner cavity is structured to define or mirror the desired shape of the shaped tampon. The inner cavity of a carrier mold may be profiled to achieve any shape known in the art including, but not limited to rectangular, triangular, curved, trapezoidal, semi-circular, hourglass, bottle, serpentine or other suitable shapes. The outer surface of the carrier mold is the surface external to the inner surface and can be profiled or shaped in any manner, such as, rectangular, cylindrical or oblong. The carrier mold may comprise a single integral structure or one or more individual separate component pieces.

The carrier mold of the present invention may be used for producing any type of shaped tampon known in the art, including but not limited to the shaped tampons disclosed in U.S. Pat. No. 6,824,536 entitled "Substantially Serpentine Shaped tampon," and U.S. Pat. No. 6,932,805, entitled "Shaped tampon." Further, the carrier mold of the present invention may be used to produce shaped tampons having secondary absorbent members, such as those disclosed in U.S. Pat. No. 6,258,075, entitled "Shaped tampon with Enhanced Leakage Protection."

As used herein, "self-sustaining" is a measure of the degree or sufficiency to which a shaped tampon retains its form after stabilization, such that in the absence of external forces, the resulting shaped tampon will tend to retain its vaginally insertable shape, length, width, or volume. For shaped tampons, it is found that control of the level of moisture within the shaped tampon is a factor for helping the shaped tampon to retain its shape, length, width, or volume subsequent the absence of the external compression forces. It will be understood by one of skill in the art that this self-sustaining form need not persist during actual use of the shaped tampon. That is, once the shaped tampon is inserted into the vagina or other body cavity, and begins to acquire fluid, the shaped tampon will begin to expand and may lose its self-sustaining form.

The term "stabilized," as used herein, refers to a shaped tampon in a self-sustaining state prior to use, wherein the shaped tampon has overcome the natural tendency to re-expand to the uncompressed pledget's original shape, length, width, or volume.

As used herein the term "shaped tampon," refers to any type of absorbent structure that is inserted into the vaginal canal or other body cavities for the absorption of fluid therefrom, to aid in wound healing, or for the delivery of active materials, such as medicaments, or moisture. A shaped tampon can have varying perimeters along its length. In certain embodiments, a shaped tampon may have a substantially serpentine shape, an "undercut" or "waist." The phrase "substantially serpentine" refers to a non-linear dimension between any two points spaced at least about 5 mm apart. The term "undercut" refers to shaped tampons having a protuberance or indentation that impedes the withdrawal of a shaped tampon from a unitary mold. For example, shaped tampons may be hourglass shaped having at least one perimeter in the center of the shaped tampon or "waist" that has a diameter less than both the smallest insertion end perimeter diameter and the smallest withdrawal end perimeter diameter. A shaped tampon may comprise an overwrap, skirt, secondary member, withdrawal member, or any combination thereof, as described previously with reference to pledgets.

Shaped tampons have an insertion end, withdrawal end, a length, perimeters, a longitudinal axis, and an exterior surface, which may be absorbent material or an overwrap. A shaped tampon's length can be measured from the insertion end to the withdrawal end along the longitudinal axis. A typical compressed shaped tampon for human use is about 30 mm to about 60 mm in length. A shaped tampon may be straight or non-linear in shape, such as having one or more curves along the longitudinal axis. In certain embodiments, a compressed shaped tampon may have a greatest perimeter of from about 25 mm to about 60.

In certain embodiments, a shaped tampon can be inserted digitally. In certain embodiments, when a shaped tampon is intended to be digitally inserted, a finger indent may be provided at the withdrawal end of the shaped tampon to aid in insertion, such as finger indents as described in U.S. Pat. No. 6,283,952. In certain embodiments, a shaped tampon can be inserted using an applicator. Any suitable applicator can be used, including, for example, tube and plunger type arrangements that can be plastic, paper, or other suitable material, and compact type applicators.

A "perimeter" is a cross-sectional distance as measured around the outer surface of a structure such as a shaped tampon, carrier mold, or secondary sleeve. A perimeter also has a perimeter diameter. The term perimeter diameter as used herein refers to the longest line segment whose endpoints are on the outer surface defining the perimeter. A perimeter may be measured, for instance, using Resin Embedded Microtome along with Scanning Electron Microscopy—S.E.M. (supplied by companies such as Resolution Sciences Corporation; Corte Madera, Calif.)

The term "longitudinal axis" is an imaginary line positioned at or near the center of an article and which traverses the length of the article.

The term "cross-section" as used herein is a planar view that intersects a structure perpendicularly to the structure's longitudinal axis.

The term "vaginal cavity" as used herein, is intended to refer to the internal genitalia of a mammalian female, such as a human female, in the pudendal region of the body, which is the space located between the introitus of the vagina, sometimes referred to as the sphincter of the vagina or hymeneal ring, and the cervix.

FIG. 1 shows a carrier mold 10 of the present invention used to produce shaped tampons. The carrier mold comprises a first end 11, a second end 13, an outer surface 12, a perimeter 50, a length L, and a longitudinal axis LA. The length L is measured along the longitudinal axis, from the first end 11 to the second end 13 of the carrier mold 10. To produce shaped tampons the carrier mold 10 comprises a body 20 and two or more prongs 30. The prongs 30 are flexible, such that when the outer surface 12 of a prong 30 is subjected to pressure, the prong 30 will flex in a general direction towards the longitudinal axis LA of the carrier mold 10. When the prongs 30 flex towards the longitudinal axis LA in response to pressure on the outer surface 12 the prongs 30 completely or substantially close the first end 11 of the carrier mold 10, thereby completely or substantially closing one end of the carrier mold's 10 inner cavity 72, allowing the carrier mold 10 to produce shaped tampons.

Figure 2:
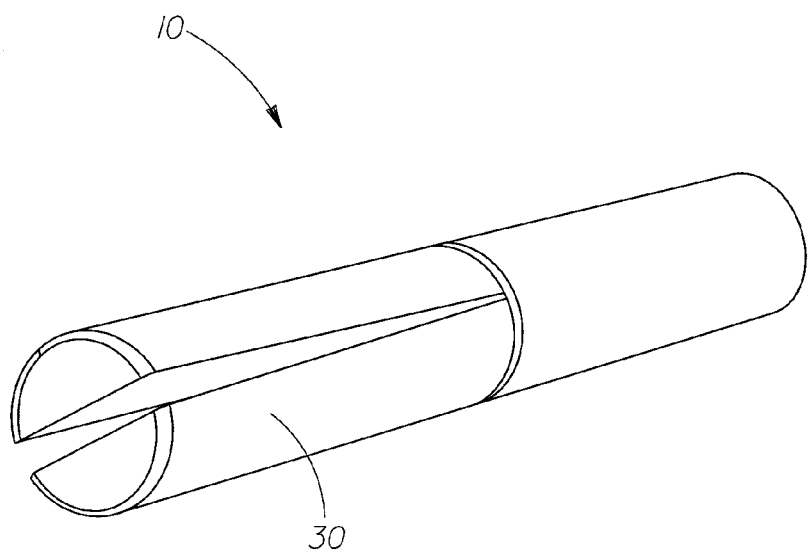
FIG. 2 is a perspective view of a carrier mold of the present invention.

A prong 30 has a proximal base 32, which is the end of a prong 30 that is closest to, attached to, or integral with the body 20 or region of weakness 14 of a carrier mold 10. A prong 30 also has a distal end 40, which is the end of a prong 30 that is the farthest distance from the body 20 of a carrier mold 10. The distal end 40 of a prong 30 may have an overhang 42, such that the overhang 42 extends in a general direction starting from the outer surface 12 of the carrier mold 10 towards the longitudinal axis LA of the carrier mold 10. The number of prongs 30 may vary. For example, a carrier mold 10 may have from two prongs 30, as shown in FIG. 2, to twenty or more prongs. In certain embodiments, a carrier mold may have from four prongs to ten prongs.

Referring back to FIG. 1, a prong 30 has a length PL and one or more arc lengths PA as measured along the outer surface 12 of the carrier mold 10. The length PL and one or more arc lengths PA of a prong 30 may be of any length PL or arc length PA suitable to provide a carrier mold 10 that has two substantially open ends, but wherein upon the application of pressure to the outer surface 12 of a prong 30, the prong 30 can flex to completely or substantially close the first end 11 of the carrier mold 10. The arc length PA of a prong 30 may vary along the length PL of a prong 30. In certain embodiments, the arc length PA of a prong 30 is less at the distal end 40 of the prong 30 as compared to the proximal base end 32 of the prong 30. In certain embodiments, the length PL of a prong 30 may be from about 10% to about 90% of the length L of the carrier mold 10 to which it is a part of In certain embodiments, the length PL of a prong 30 may be from about 30% to about 70% of the length L of the carrier mold 10 to which it is a part of In certain embodiments, the largest arc length PA dimension of a prong 30 may be from about 5% to about 50% of the largest perimeter 50 of the carrier mold 10 to which it is a part of In certain embodiments, the largest arc length PA dimension of a prong 30 may be from about 25% to about 10% of the largest perimeter 50 of the carrier mold 10 to which it is a part of.

Figure 3:
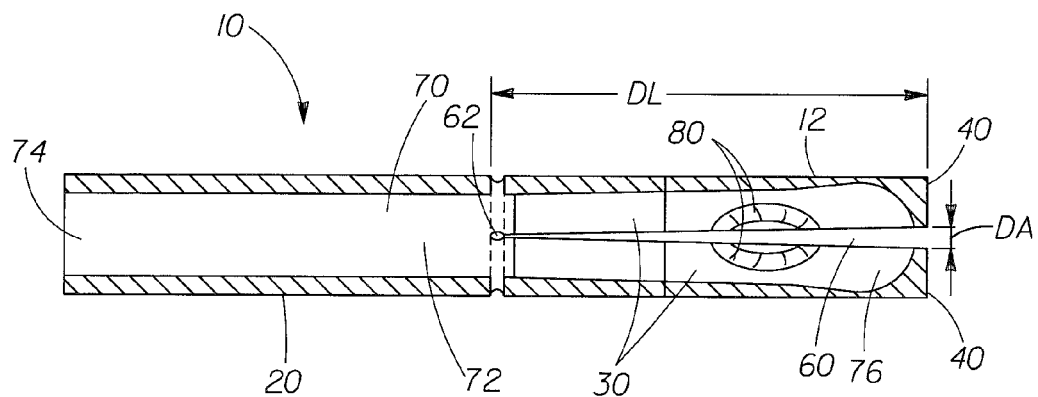
FIG. 3 is a longitudinal cross-sectional view of a carrier mold of the present invention.
Figure 4:
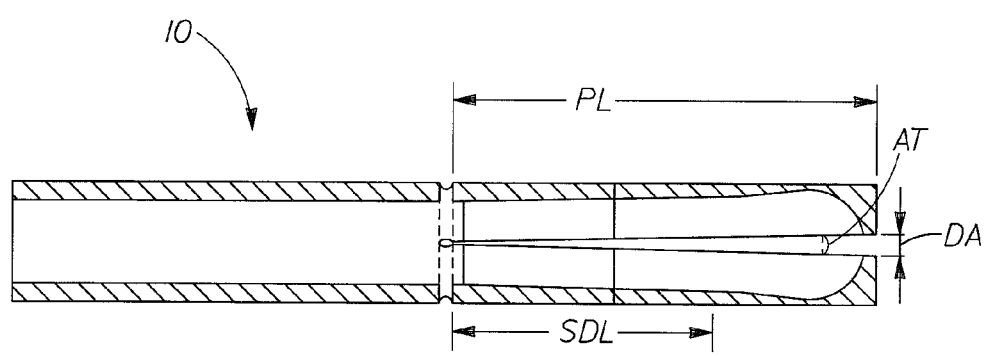
FIG. 4 is a longitudinal cross-sectional view of a carrier mold of the present invention.
Figure 5:
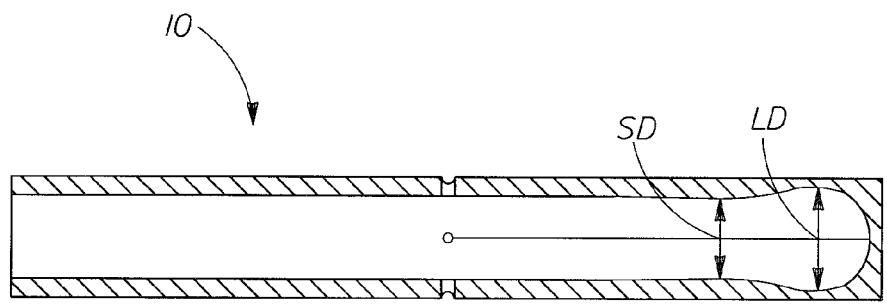
FIG. 5 is a longitudinal cross-sectional view of a carrier mold of the present invention.

As shown in FIG. 3, a prong 30 is separated from another prong 30 by a discrete space 60. A discrete space 60 has a maximum arc length DA, which in certain embodiments is positioned at or near the distal ends 40 of two prongs 30. The maximum arc length DA of a discrete space 60 is the greatest distance between two adjacent prongs 30 as measured from the outer surface 12 of the carrier mold 10. A discrete space 60 also has a length DL as measured from the distal end 40 of the prongs 30 to the body 20 of the carrier mold 10. In certain embodiments, a vertex end 62 of a discrete space 60, which is positioned at or near the body 20, instead of coming to a point may be expanded in such a manner as to increase the flexibility of the prongs 30. Such an expansion of the vertex end 62 may have any suitable shape to provide greater flexibility to a prong 30, as observed from the outer surface 12 of the carrier mold 10, such as circular, elliptical, triangular, quadrangular, or any other useful shape. Further, the determination of the maximum arc length DA of a discrete space 60 may be determined using the following formula, as shown in FIG. 4 and FIG. 5:

$$DA = 2*\pi*PL*(AT/360)$$
Wherein:
AT (arc length of travel) = $2\theta$
$\theta = ([(AD + CL)/(2*SDL)])\tan^{-1}$
$AD = LD - SD$
$CL = ED - LD$ SD = smallest diameter of the inner cavity*;
CL = clearance
LD = largest diameter of the inner cavity*;
ED = exit/entry diameter of the inner cavity*;
SDL = distance from prong proximal base to SD;
PL—prong length;
*Diameter of the inner cavity refers to the longest line segment whose endpoints are within a cross-section of the inner cavity as defined by the carrier mold inner surface.

Figure 6:
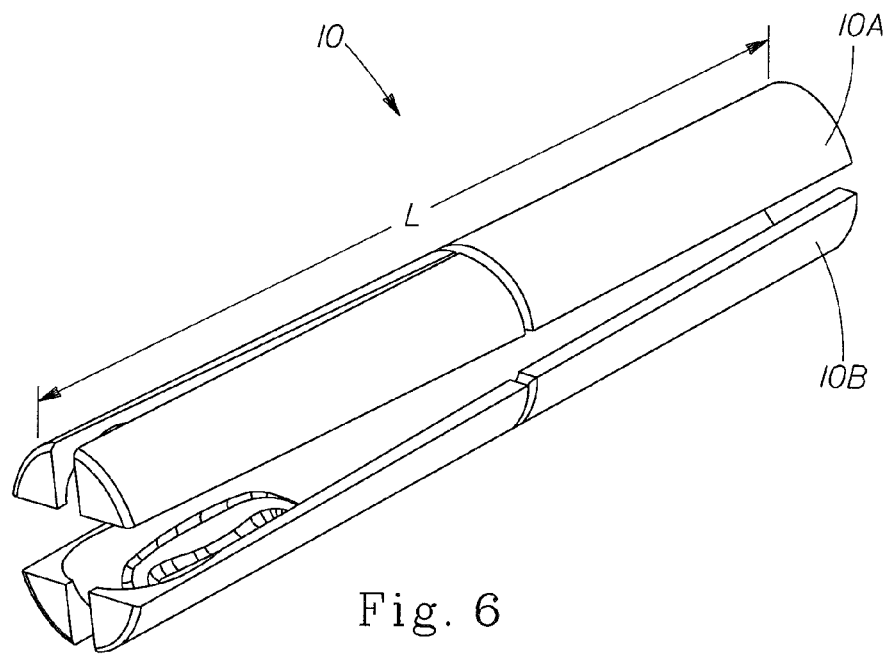
FIG. 6 is a perspective view of a carrier mold of the present invention.

In certain embodiments, a carrier mold may comprise a single integral structure. For example, the prongs and body of a carrier mold may be formed from the same material at or around the same time, for instance by one of the following methods, such as by molding, machining, stereolithography, or the like, thereby creating a single integral structure. In certain other embodiments, a carrier mold may be comprised of one or more individual separate component pieces. For example, one embodiment of a carrier mold 10 having two component pieces is shown in FIG. 6. In FIG. 6 the carrier mold 10 comprises two component pieces 10A and 10B that are separated along the length L of the carrier mold 10. In other embodiments, the component pieces of a carrier mold 10 may comprise one or more prongs 30 that are separate from the body 20 of a carrier mold 10. The one or more prongs may be attached to the body of a carrier mold by any method known in the art, for example mechanically, by bonding, or through the use of hinges. Further, the component pieces of a carrier mold may be comprised of the same or different materials.

A carrier mold may be formed from one or more materials. Materials for the carrier mold may include metals, polymers or composites. Embodiments of the carrier mold that are comprised of metals may include steel, stainless steel, copper, brass, titanium, alloys, aluminum, anodized aluminum, and combinations thereof. Embodiments of the carrier mold that are comprised of polymers may include TEFLON® (E.I du Pont de Nemours and Company; Wilmington, Del. USA), polyethylene, polypropylene, polyester, polyolefins, polycarbonates, nylons, polyvinyl chloride, polybutylene terephthalate, and mixtures thereof. One embodiment of a carrier mold may be made of DELRIN® (E.I du Pont de Nemours and Company; Wilmington, Del. USA). Carrier mold embodiments that are comprised of composites may include carbon fibers and blends of metal, epoxy, ceramic and polymer blends. Other examples of suitable materials for a carrier mold are foamed metals or plastics. A carrier mold may be made of aluminum and epoxy porous aggregate, such as METAPOR BF100A1 (Portec Ltd, Switzerland). In certain embodiments, a carrier mold may have one or more coatings, for example a carrier mold may have a coating that aids in release, such as TEFLON®.

Referring back to FIG. 1, in certain embodiments, one or more regions of weakness 14 may be present on or in the carrier mold 10, and positioned between the proximal base 32 of one or more prongs 30 and the second end 13 of the carrier mold 10. As used herein, the term "region of weakness" refers to a region of the carrier mold 10 that provides a prong 30 with greater flexibility (as compared to a prong lacking a region of weakness), in response to pressure, by allowing the prong 30 to more freely flex. A region of weakness can extend in one or more directions, for example a region of weakness can be straight, bent, angled, curved, irregular or combinations thereof.

In certain embodiments, a region of weakness may have a thickness that is substantially less than the thickness of the carrier mold that surrounds the region of weakness, but greater than zero, for example a depression. In certain embodiments, individual depressions can overlap each other when forming a line of weakness, so that a substantially continuous region of weakness formed by depressions is produced, such as a score line or groove, as shown by the region of weakness 14 in FIG. 1. In certain embodiments, a region of weakness may be formed by having one or more gaps, in the form of material separations, between a prong and body of the carrier mold, such that a gap can have a thickness of about zero. The gaps may take many forms including perforations or slits. A region of weakness can be formed in any suitable manner, such as mechanically, thermally, using a laser, chemically, or combinations thereof.

The cross-sectional shape of the carrier mold 10 outer surface 12 can be any suitable shape such as circular, elliptical, triangular, square, or rectangular. The cross-sectional shape of the carrier mold 10 outer surface 12 may be substantially the same along the length of the carrier mold 10, the cross-sectional shape of the carrier mold 10 outer surface 12 may vary along the length of the carrier mold 10, or combinations of both. For example, in certain embodiments the carrier mold 10 outer surface 12 formed by the prongs 30 may differ from the cross-sectional shape of the outer surface 12 of the body 20.

As shown in FIG. 3, a carrier mold 10 comprises an inner surface 70, wherein the inner surface 70 defines an inner cavity 72 for shaping a pledget during compression or retaining the shape of a shaped tampon subsequent to compression, for example during the stabilization process. A shaped tampon may be stabilized within the inner cavity 72 by any known method, for example through the use of heat, steam, or radiation. The inner cavity 72 has an open proximal end 74 and an intermittently closed distal end 76. In certain embodiments of the carrier mold 10, the open proximal end 74 is used for both an ingress port where a pledget, compressed or otherwise, is introduced into the inner cavity 72 and as an evacuation port where a shaped tampon can be evacuated from the inner cavity 72.

Figure 7:
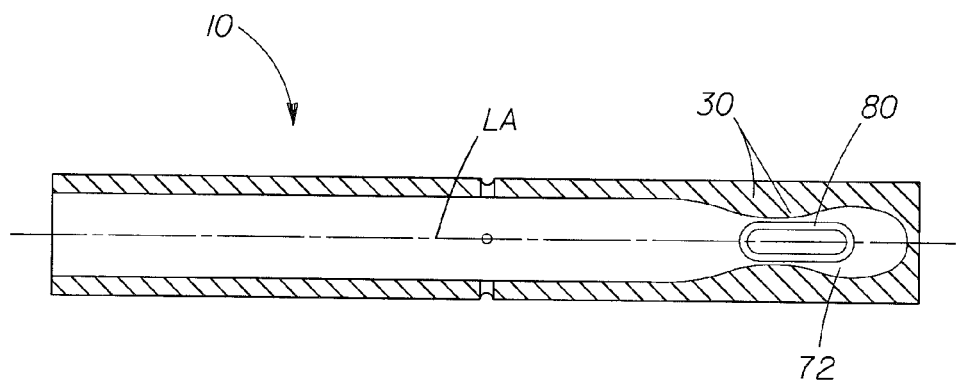
FIG. 7 is a longitudinal cross-sectional view of a carrier mold of the present invention.
Figure 8:
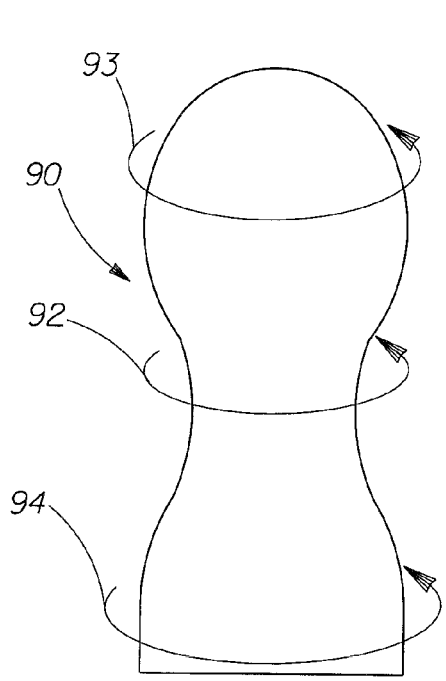
FIG. 8 is a perspective view of a shaped tampon produced using a carrier mold of the present invention.
Figure 8A:
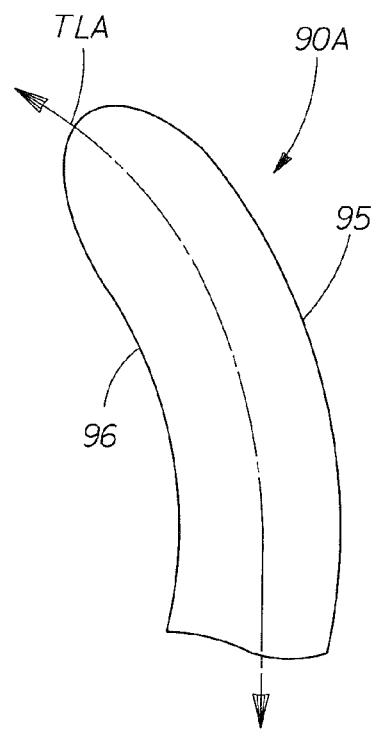
FIG. 8A is a perspective view of a shaped tampon produced using a carrier mold of the present invention.

When two or more prongs 30, as shown in FIG. 7, are brought into contact with one another through flexing they serve to completely or substantially close the intermittently closed distal end 76 of the inner cavity 72, thereby completing the inner cavity 72 of the carrier mold 10. The shape of the closed inner cavity 72 determines the shape of the shaped tampon. The closed inner cavity 72 of the carrier mold 10 can produce any suitable shaped tampon. For example, in certain embodiments, as shown in FIG. 8, a shaped tampon 90 may be hourglass shaped having an undercut 92. Wherein, in certain embodiments the undercut 92 comprises at least one perimeter in the center of the shaped tampon or "waist" having a diameter that is less than a perimeter diameter of the insertion end 93 and a perimeter diameter of the withdrawal end 94. Further, as shown in FIG. 8A, a carrier mold may produce a shaped tampon 90 that is curved along the longitudinal axis TLA. The longitudinal axis TLA is flanked by a major radius of curvature 95 and a minor radius of curvature 96. The major radius of curvature 95 is formed on a radius that is larger than the radius on which the minor radius of curvature 96 is formed.

Referring back to FIG. 3, in certain embodiments, the inner surface 70 may have one or more marking means 80, such as projections or recesses, which can produce one or more patterns on or in the exterior surface of a shaped tampon. For example, projections will produce an indentation and a recess will produce a protrusion on the exterior surface of a shaped tampon. A marking means 80 may span more than one prong 30, as shown in FIG. 3, or a marking means may be present on a single prong. A marking means may include combinations of projections and recesses. There may be more than one marking means present on the inner surface of a carrier mold. If there is more than one marking means present the marking means may be arranged to provide a pattern or texture on the exterior surface of a shaped tampon. Further, in certain embodiments, the inner surface of a carrier mold may have longitudinally-extending projections in the form of ridges or longitudinally-extending recesses in the form of grooves to form a shaped tampon having longitudinally-oriented "flutes" that can be generally straight or can be in a generally spiral orientation along the length of a shaped tampon.

A marking means can be any suitable size. In certain embodiments, a marking means may produce a pattern that covers less than the entire exterior surface of a shaped tampon, for example less than about 75% of the exterior surface, less than about 50% of the exterior surface, less than about 40% of the exterior surface, less than about 30% of the exterior surface, less than about 20% of the exterior surface, or less than about 10% of the exterior surface of a shaped tampon.

A marking means, whether a projection, recess, or combinations of both can be any suitable form for providing the exterior surface of a shaped tampon with one or more patterns, such as a rectangle, a square, a circle, an oval, an ellipse, a triangle, a crescent, a chevron, a diamond, a trapezoid, an hourglass, a flower, a star, a groove, a ridge, a line, a rain drop, a peanut, a wave, a dimple, cross-hatching, a polygon, a petal, a letter, a number or any other suitable shape. In certain embodiments, as shown in FIG. 3 a marking means may have a pre-flexural form 80 prior to two or more prongs 30 flexing to completely or substantially close the inner cavity 72 of the carrier mold 10. As shown in FIG. 7 the final form of a marking means 80, which will provide the desired pattern on or in the exterior surface of a shaped tampon, is not produced until two or more prongs 30 flex to completely or substantially close the inner cavity 72 of the carrier mold 10. A marking means may be present on any suitable location of the inner surface of a carrier mold, to provide a pattern on or in a shaped tampon. For example, a marking means may be present on the inner surface so as to provide a pattern to the insertion end of a shaped tampon, the withdrawal end of a shaped tampon, or any other suitable location.

In certain embodiments, a pattern provided to the exterior surface of a shaped tampon, may be in the form of a benefit indicator. A benefit indicator can be used to communicate to a user, benefits of the shaped tampon, such as absorbency level, protection features, comfort features, softness features, or other features, for example softness, scent, lubrication, an absorbent core, layers, a secondary absorbent, an overwrap, channels, grooves, protrusions, apertures, or a skirt. Such benefit indicators can allow a user to become aware of the benefits and features of the shaped tampon while viewing the shaped tampon itself. Benefit indicators, can further provide a user with confidence in their choice of leakage protection or can reduce the anxiety a user may feel regarding leakage. In certain embodiments, the benefit indicator can be visible pre-use to the user. In addition, or alternatively, all or a portion of the benefit indicator can be visible post-use, for example after expansion or removal of the shaped tampon.

The length of a carrier mold can vary. In certain embodiments, the length of a carrier mold can vary from about 30 mm to about 400 mm. In certain other embodiments, the length of a carrier mold can vary from about 50 mm to about 200 mm. The perimeter of a carrier mold can also vary. In certain embodiments, the perimeter of a carrier mold can vary from about 8 mm to about 50 mm. In certain other embodiments, the perimeter of a carrier mold can vary from about 12 mm to about 25 mm. Further, the perimeter of a carrier mold can vary along the length of the carrier mold.

Figure 9:
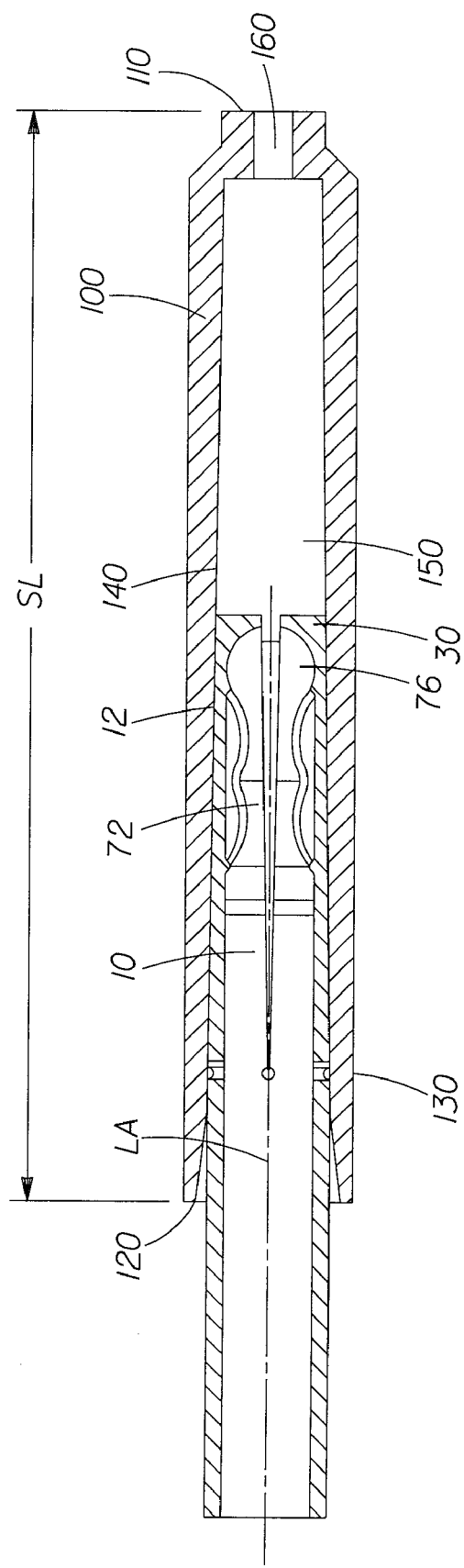
FIG. 9 is a longitudinal cross-sectional view of a secondary sleeve and carrier mold combination of the present invention.
Figure 10:
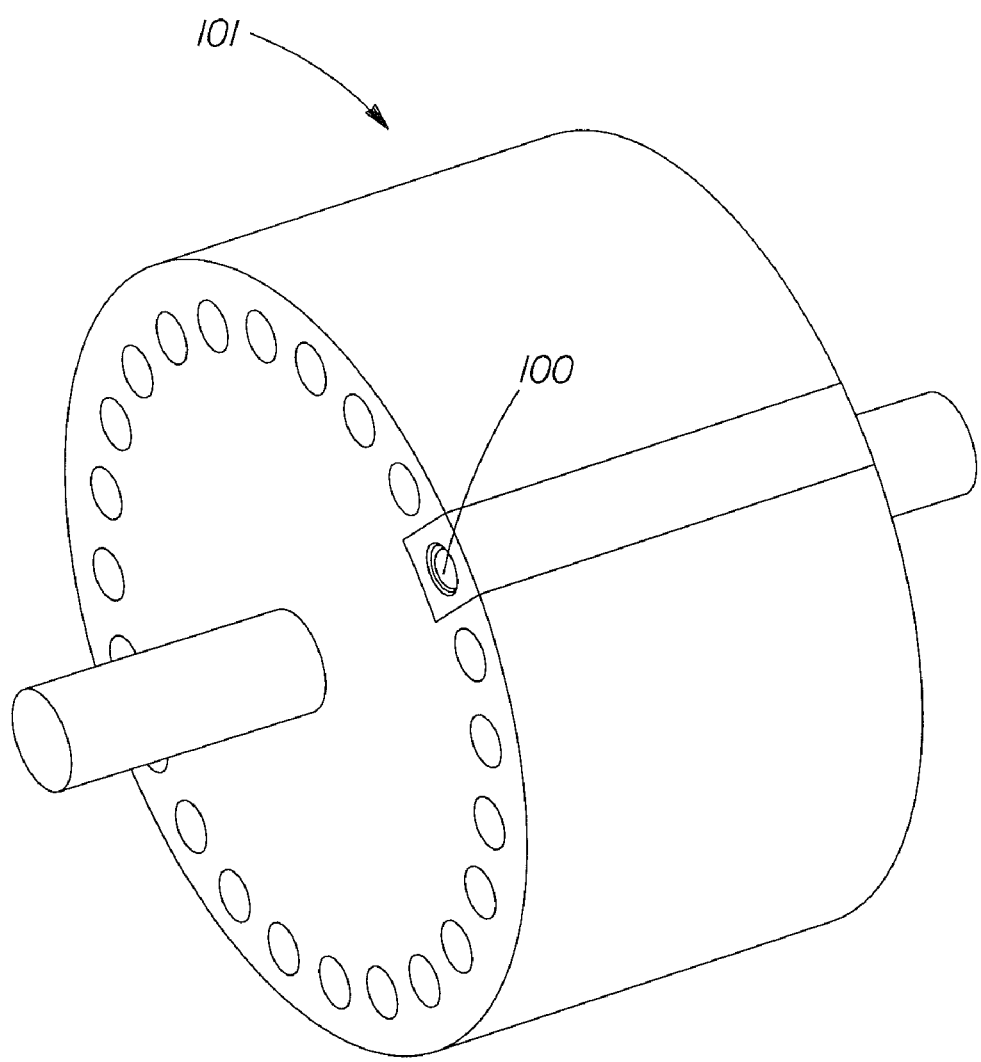
FIG. 10 is a perspective view of a drum of the present invention.

As shown in FIG. 9, to produce a shaped tampon a carrier mold 10 may be inserted into a secondary sleeve 100 to provide a carrier mold 10 and secondary sleeve 100 combination. A secondary sleeve 100 comprises a pushrod end 110, an evacuation end 120, an outer surface 130, an inner surface 140, an inner space 150, a pushrod opening 160, and a length SL. The secondary sleeve 100 may be a carrying member. A secondary sleeve may be formed from one or more materials. Materials for the secondary sleeve may include metals, polymers or composites. Embodiments of the secondary sleeve that are comprised of metals may include steel, stainless steel, copper, brass, titanium, alloys, aluminum, anodized aluminum, and combinations thereof. Embodiments of the secondary sleeve that are comprised of polymers may include TEFLON® (E.I du Pont de Nemours and Company), polyethylene, polypropylene, polyester, polyolefins, polycarbonates, nylons, polyvinyl chloride, polybutylene terephthalate, and mixtures thereof. One embodiment of a secondary sleeve may be made of DELRIN®) made by DuPont Plastics (Wilmington, Del. USA). Embodiments of a secondary sleeve that are comprised of composites may include carbon fibers and blends of metal, epoxy, ceramic and polymer blends. Other examples of suitable materials for the secondary sleeve are foamed metals or plastics. Further, a secondary sleeve may be made of aluminum and epoxy porous aggregate, such as METAPOR BF100A1, available from Portec Ltd, Switzerland. The cross-sectional shape of the secondary sleeve outer surface can be any suitable shape such as circular, elliptical, triangular, square, or rectangular. The cross-sectional shape of the secondary sleeve outer surface may be substantially the same along the length of the secondary sleeve, the cross-sectional shape of the secondary sleeve outer surface may vary along the length of the secondary sleeve, or combinations of both. Further, a secondary sleeve 100 may be part of or disposed within a drum 101, as shown in FIG. 10.

With reference back to FIG. 9, the secondary sleeve 100 inner surface 140 defines the inner space 150. The secondary sleeve 100 inner space 150 can be any shape or dimension suitable to allow a carrier mold 10 to be inserted into the inner space 150 and to provide pressure to the outer surface 12 of the prongs 30 of the carrier mold 10, causing the prongs 30 to flex towards the longitudinal axis LA to completely or substantially close the intermittently closed distal end 76 of the carrier mold 10 inner cavity 72, thereby completing the inner cavity 72 of the carrier mold 10. A carrier mold 10 may be completely or partially disposed within the inner space 150 of the secondary sleeve 100. As shown in FIG. 11, in certain embodiments, as the inner space 150 extends towards the push rod end 110 the inner space 150 assumes a generally conical shape, such that the diameter of the inner space 150 decreases towards the pushrod end 110. Wherein the diameter of the inner space refers to the longest line segment whose endpoints are within a cross-section of the inner space as defined by the secondary sleeve inner surface. Therefore, as the carrier mold 10 travels towards the pushrod end 110 of the secondary sleeve 100 the diameter of the inner space 150 decreases, providing pressure to the outer surface 12 of the prongs 30 of the carrier mold 10. The pressure causes the prongs 30 to flex towards the longitudinal axis LA of the carrier mold 10, and the farther the carrier mold 10 travels towards the pushrod end 110 of the secondary sleeve 100 the greater the prongs 30 flex towards the longitudinal axis LA, so as to completely or substantially close the carrier mold 10 inner cavity 72, thereby completing the inner cavity 72 of the carrier mold 10. The secondary sleeve 100 inner space 150 does not have to assume a generally conical shape to flex the prongs 30 of the inner cavity member 10. For example, in certain embodiments, as shown in FIG. 12 the secondary sleeve 100 inner space 150 may have one or more protuberances 152 that serve to flex the prongs 30 of the inner cavity member 10.

As shown in FIG. 13, the secondary sleeve 100 includes a pushrod opening 160. The pushrod opening 160 is positioned at the pushrod end 110 of the secondary sleeve 100, and extends from the secondary sleeve 100 outer surface 130 to the secondary sleeve 100 inner space 150. The pushrod opening 160 can be any suitable dimension to allow a pushrod 170 to enter the secondary sleeve 100 inner space 150. As shown in FIG. 13, a pushrod 170 enters the pushrod opening 160 and contacts the first end 11 of the carrier mold 10. FIG. 14 shows the pushrod 170 moving the carrier mold 10 towards the evacuation 120 end of the secondary sleeve 100. As the pushrod 170 moves the carrier mold 10 towards the evacuation end 120 of the secondary sleeve 100 the pressure on the outer surface 12 of the prongs 30 lessens as the diameter of the inner space 150 increases. The movement of the carrier mold 10 away from the narrower pushrod end 110 of the inner space 150 allows the prongs 30 to separate from one another and resume an unflexed position, thereby opening the carrier mold 10 inner cavity 72. The separation of the prongs 30 increases the volume of the inner cavity 72 and results in the inner surface 70 of the inner cavity 72 reducing its contact with the shaped tampon 90, such that the smallest diameter of the inner cavity 72 will not significantly impede the movement of the shaped tampon 90 towards the second end 13 of the carrier mold 10. The opening to the inner cavity 72 allows the push rod 170 to enter the inner cavity 72 and contact a shaped tampon 90. FIG. 15 shows that after the push rod 170 contacts the shaped tampon 90 the pushrod 170 moves the shaped tampon 90 towards the second end 13 of the carrier mold 10, and in certain embodiments the pushrod 170 expels the shaped tampon 90 from the carrier mold 10.

As shown in FIG. 16, in certain embodiments, the end 172 of the pushrod 170 that enters the inner cavity 72 of the carrier mold 10 may be shaped to reduce possible impact damage to the first end 11 of the carrier mold 10, specifically the overhang 42 of the prongs 30. For example, in the embodiment shown in FIG. 16, the end 172 of the pushrod 170 has been beveled to ease the insertion of the pushrod 170 into the inner cavity 72 of the carrier mold 10. The end 172 of the pushrod 170 that enters the carrier mold 10 may be any suitable shape for reducing possible impact damage to the carrier mold 10, such as conical or semi-hemispherical In addition to or as an alternative to a pushrod 170 having a shaped end 172, the prong 30 overhangs 42 of the carrier mold 10 may also be shaped to reduce possible impact damage to the carrier mold 10. For example, the overhangs 42 may be beveled to allow the pushrod 170 easier access to the inner cavity 72 of the carrier mold 10 or the thickness "T" of an overhang 42 may be adjusted to reduce the impact damage caused by the pushrod 170. The thickness "T" of an overhang 42 may be determined by factors such as the material used to produce an overhang; the speed with which a pushrod contacts an overhang; type of shaping for an overhang, for example if the overhang is beveled what is the degree to which the overhang has been beveled; or the material used to produce a pushrod.

Figure 17:
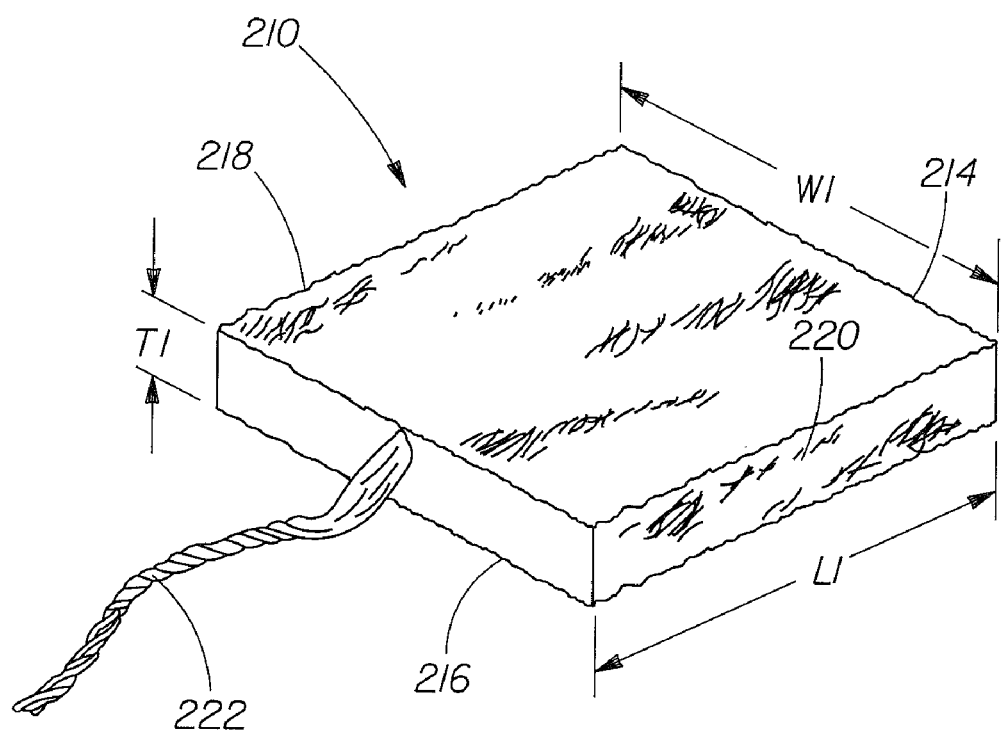
FIG. 17 is a perspective view of a pledget for use in making a shaped tampon in accordance with an embodiment of the present invention.

The carrier mold of the present invention can be used to produce a shaped tampon from a pledget. For example, turning to FIG. 17 a pledget 210 of absorbent material is shown. The pledget 210 may be compressed and then shaped using a carrier mold to produce a shaped tampon in accordance with an embodiment of the present invention. The pledget 210 extends from an insertion end 214 to a withdrawal end 216 with opposing sides 218 and 220 extending from the insertion end 214 to the withdrawal end 216. A withdrawal member 222 may be connected to and extend from the withdrawal end 216 of the pledget 210.

Although the pledget 210 is shown as having a generally square or rectangular shape, the pledget 210 can have a variety of shapes, including, but not limited to, oval, round, chevron, square, rectangular, trapezoidal, and the like. The pledget 210 may have a length L1 extending from the insertion end 214 to the withdrawal end 216 of the pledget 210, a width W1 extending from the one side 218 of the pledget 210 to the other side 220 and perpendicularly to the length L1, and a thickness T1 extending perpendicularly to both the length L1 and width W1 of the pledget 210.

Figure 18:
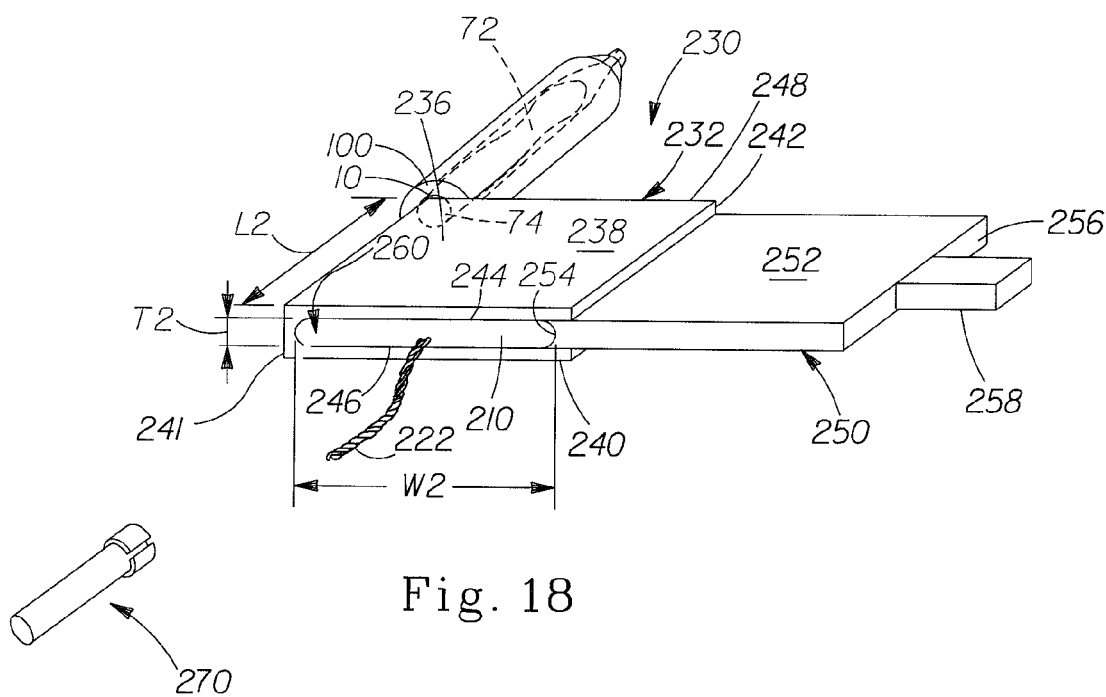
FIG. 18 is a perspective view of a shaped tampon producing apparatus.
Figure 19:
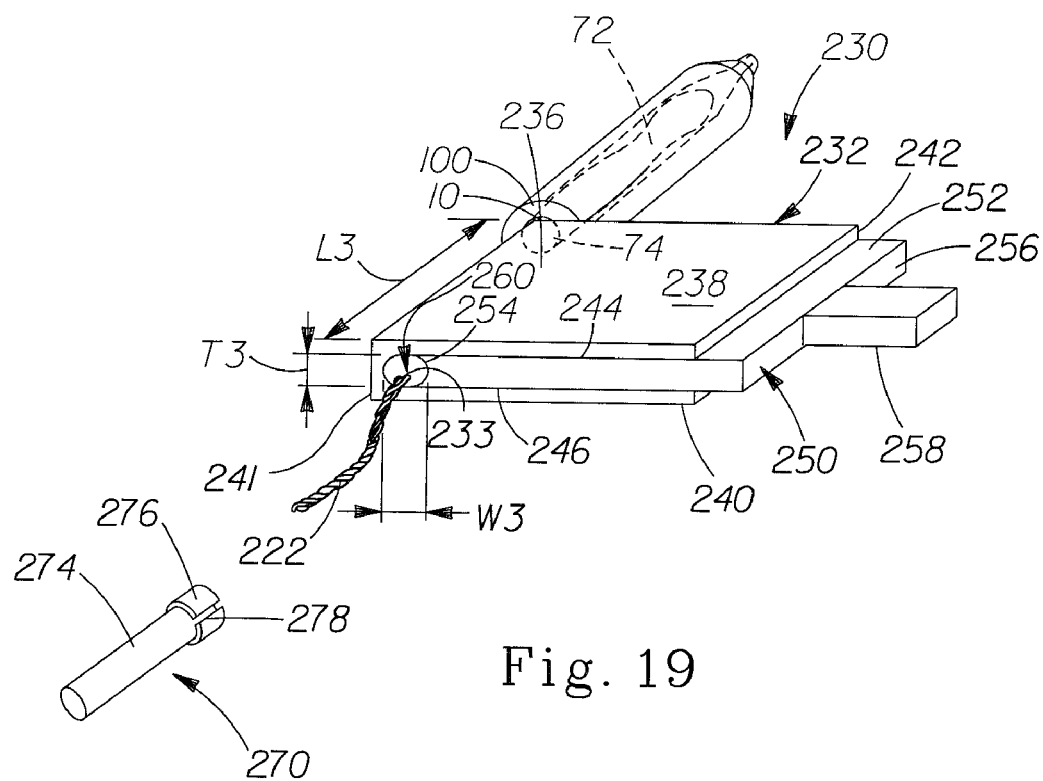
FIG. 19 is a perspective view of a shaped tampon producing apparatus.
Figure 20:
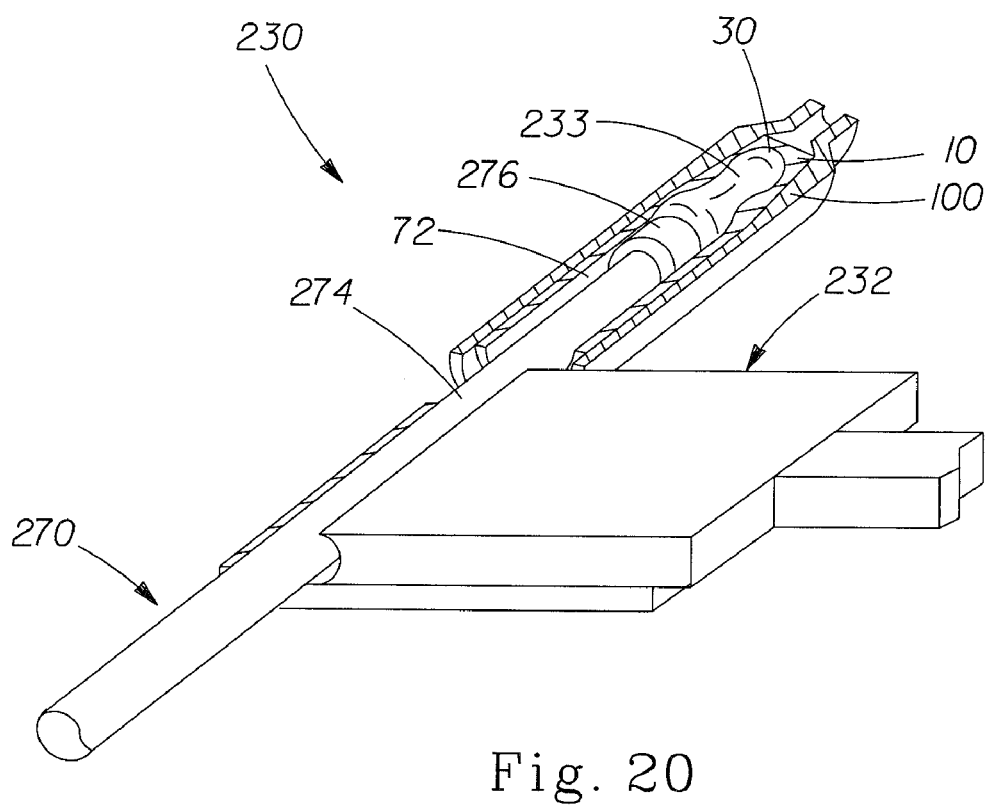
FIG. 20 is a partial perspective view of a shaped tampon producing apparatus.

A shaped tampon producing apparatus 230 for making shaped tampons in accordance with an embodiment of this invention is shown in FIG. 18 to FIG. 20. The shaped tampon producing apparatus 230 may generally comprise a compression machine 232 for initially compressing the pledget 210 of absorbent material to provide a compressed pledget 233, a carrier mold 10 for receiving the compressed pledget 233 and molding the compressed pledget 233 into a shaped tampon, a secondary sleeve 100, and a compression member 270 for transferring the compressed pledget 233 into the carrier mold 10.

The compression machine 232 may comprise a u-shaped anvil 236. The compression machine 232 may comprise a top plate 238 and a juxtaposed bottom plate 240 extending from an end wall 241 connecting the top plate 238 and bottom plate 240 to an open end 242 thereby forming a channel 244 between the top plate 238 and bottom plate 240. The channel 244 may extend from an inlet end 246 to a discharge end 248 of the anvil 236. The compression machine 232 may also comprise a die 250 comprising a solid plate 252 extending from a leading end 254 to a trailing end 256 and an actuating rod 258 connected to the trailing end 526 for reciprocating the die 250 within the channel 244 of the anvil 236. The leading end 254 of the die 250, top plate 238, bottom plate 240 and end wall 241 of the anvil 236 may form a compression machine cavity 260 within the channel 244 of the anvil 236 for receiving the pledget 210. The die 250 may compress the pledget 210 in the compression machine cavity to provide the compressed pledget 233. Other configurations for the compression machine 232 for carrying out the functions described herein will be apparent to those skilled in the art from reading the details of this specification.

When in an open configuration as illustrated in FIG. 18, the compression machine cavity 260 may have a length L2 extending from the inlet end 246 of the anvil 236 to the discharge end 248, a width W2 extending from the interior of the anvil end wall 241 to the leading end 254 of the die 250 and perpendicular to the length L2, and a thickness T2 extending from the interior of the top plate 238 of the anvil 236 to interior of the bottom plate 240 perpendicular both to the length L2 and width W2 of the compression machine cavity 260. In certain embodiments, the width W2 of the compression machine cavity 260 when the compression machine cavity 260 is in an open configuration may be close to or greater than the width W1 of the pledget 210. In certain embodiments, the length L2 of the compression machine cavity 260 may also be close to or greater than the length L1 of the pledget 210.

When in a compression configuration as illustrated in FIG. 19, the compression machine cavity 260 may have a length L3 which is the same as the length L2 in the open configuration and a thickness T3 which is same thickness as T2 in the open configuration, but may have a width W3 which may be substantially less than the width W2 of the compression machine cavity 260 in the open configuration and may be substantially less than the width W1 of the pledget 210. In certain embodiments when the pledget 210 is compressed in the compression machine 232, the compressed pledget 233 may assume the cross-sectional shape and width and thickness of the compression machine cavity 260 in the compressed configuration. As such, the compressed pledget 233 may have a width of W3 and a thickness of T3. The manner of actuation of the die 250 within the anvil channel 244 to compress the pledget 210 may be by any suitable means to drive the actuating rod 258.

The degree of compression of the pledget 210 in the compression machine cavity 260 in the widthwise direction may be a major component of the compression. In accordance with certain embodiments of this invention, the major compression of the uncompressed pledget in the compression machine cavity 260 in the widthwise direction is within a range from about 65% to about 90% of the original width of the pledget 210. The degree of compression of the pledget 210 in the thickness and lengthwise directions may be a minor component of the compression, and in accordance with certain embodiments of this invention, the minor compression of the pledget 210 in the compression machine cavity 260 in the thickness direction may be no more than about 60% to about 90% of the original thickness of the pledget 210 and in the lengthwise direction may be no more than about 60% to about 90% of the original length of the pledget 210. In certain embodiments, there may be no compression of the pledget 210 in the lengthwise direction or thickness direction.

As shown in FIG. 19 the inner cavity 72 open proximal end 74 of a carrier mold 10 may be aligned with the compression machine cavity 260. The inner cavity 72 open proximal end 74 may generally have a cross-sectional shape similar to the cross-sectional shape of the compression machine cavity 260 when in the compressed configuration. Because the cross-sectional shape and dimensions of the compression machine cavity 260 and the compressed configuration are very similar to the cross-sectional shape and dimensions of the inner cavity 72 open proximal end 74, the compressed pledget 233 may not expand or otherwise change shape significantly when inserted directly from the compression machine cavity 260 into the inner cavity 72 open proximal end 74.

As shown in FIG. 19, a compression member 270 may comprise an actuating rod 274 and a head 276 connected to the actuating rod 274 for contacting the compressed pledget 233 to transfer the compressed pledget 233 from the compression machine cavity 260 into the inner cavity 72 open proximal end 74. The cross-sectional shape of the compression member head 276 may be similar to and, in certain embodiments, substantially identical to the cross-sectional shape of the compression machine cavity 260 in the compressed configuration and the cross-sectional configuration of the inner cavity 72 open proximal end 74. The compression member head 276 may have a slot 278 therein for receiving the withdrawal cord 222 of the compressed pledget 233 so that the withdrawal cord is not cut by the compression member head 276 when the compression member head 276 transfers the compressed pledget 233 into the inner cavity 72 open proximal end 74.

Accordingly, the compressed pledget 233, the compression machine cavity 260 in the compressed configuration, the inner cavity 72 open proximal end 74, and the compression member head 276, each may have cross-sectional shapes and dimensions which are very similar. These close tolerances may help avoid trapping fibers from the compressed pledget 233 as the compression member head 276 transfers the compressed pledget 233 into the inner cavity 72 open proximal end 74. Trapped fibers may create binding and shearing forces that may damage the compression machine 232 or tear or otherwise damage the compressed pledget 233, or both. In certain embodiments, the compressed pledget 233, the compression machine cavity 260 in the compressed configuration, and the compression member head 276, each may have cross-sectional shapes and dimensions which are very dissimilar and, in certain embodiments, even substantially non-identical. In these instances, coordination between the compression member head 276 and the compression machine cavity 260 should be controlled to minimize or otherwise prevent damage to the shaped tampon forming apparatus 230 or the compressed pledget 233, or both, when the compressed pledget 233 is removed from the compression machine cavity 260.

In certain embodiments, the compressed pledget 233 may be heated in the inner cavity 72 of the carrier mold 10 to impart a self-sustaining shape to the compressed pledget 233 and resulting shaped tampon. Methods of setting or stabilizing a shaped tampon shape are well known and include heating the compressed pledget 233 with steam as disclosed in U.S. patent application Ser. No. 10/887,645 or thermal temperature gradient conduction or microwaving, as disclosed in U.S. Pat. No. 7,047,608.

A variety of materials may be used to make the components of the shaped tampon forming apparatus 230. Suitable materials may be relatively rigid and include, but are not limited to stainless steel, and in the case of microwave heat stabilization, microwave safe materials.

A shaped tampon may be made in accordance with an embodiment of this invention by first inserting the pledget 210 in the open compression machine cavity 260 as shown in FIG. 18. As described previously, the thickness T1 of the pledget 210 may be very close to the thickness T2 of the compression machine cavity 260 and the width W1 of the pledget 210 may be close to or less than the width W2 of the compression machine cavity 260. The length L1 of the pledget 210, however, may be less than the length L2 of the compression machine cavity 260.

As shown in FIG. 19, the pledget 210 may then be compressed in the compression machine cavity 260 by actuating the die 250 of the compression machine 232 within the anvil channel 244 toward the end wall 241 of the anvil 236 until the compressed configuration is reached. The amount of force required to compress the pledget 210 may vary but suitable forces typically are about 50 psi to about 1000 psi. A variety of techniques for actuating the compression die 250 are well known and may include, but are not limited to a modified compression machine available from Tory Engineering Company, of Osaka, Japan. According to certain embodiments, the compressed pledget 233 width W3 is predetermined and the compression machine 232 compresses the pledget 210 only to the compressed pledget 233 width W3. In accordance with certain embodiments, methods for stopping the compression applied by the die 250 may include, but are not limited to a stop or détente structure for stopping forward movement of the die 250 when the predetermined compressed pledget width W3 is reached or suitable controls on the actuating mechanism for reciprocating the die 250.

After compression in the compression machine 232, the compressed pledget 233 may be ejected from the compression machine cavity 260 by actuating the compression member 270 so that the compression member head 276 enters the inlet end 246 of the compression machine cavity 260 and extends through the compression machine cavity 260 forcing the compressed pledget 233 through the inner cavity 72 open proximal end 74.

As shown in FIG. 20, when the compressed pledget 233 initially enters the inner cavity 72 of the carrier mold 10, the compressed pledget 233 may be forced into the inner cavity 72 until the compressed pledget 233 compacts against the closed distal end 76 of the inner cavity 72 and the compressed pledget 233 is completely within the inner cavity 72. Generally, the compressed pledget 233 may be compressed by the compression machine 232 to a predefined size depending on the shape as determined by the inner cavity 72. In certain embodiments, the compressed pledget 233 may be compressed to match or approximate the smallest diameter of the inner cavity 72, for example the "waist" portion of an inner cavity 72 designed to produce hourglass shaped tampons. When the compressed pledget 233 is forced into the inner cavity 72, the compressed pledget 233 may expand slightly to fill the portions of the inner cavity 72 having diameters larger than the compressed pledget 233 as it entered the inner cavity 72. In certain embodiments, the compressed pledget 233 may be compressed to match or approximate the largest diameter of the inner cavity 72. Once in the inner cavity 72, the compressed pledget 233 may be stabilized by any means known in the art and then ejected from the inner cavity 72 using a pushrod as described previously with reference to FIG. 13 to FIG. 16

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. A carrier mold comprising:
   an outer surface, an inner surface, a first end, a second end opposite the first end, a length, a body, and at least two prongs, each prong having a proximal base, a distal end, and a length;

wherein the length of each prong is from about 30% to about 90% of the length of the carrier mold;

wherein the at least two prongs are separated by a discrete space;

wherein the inner surface defines an inner cavity for forming shaped tampons, wherein the shaped tampons have a length and comprise varying perimeters along their length, and wherein the inner cavity is structured to define a desired shape of the shaped tampons; and wherein the carrier mold first end is completely closed when the at least two prongs are in a closed position, allowing the carrier mold to produce shaped tampons.

2. The carrier mold of claim 1, wherein the carrier mold includes a region of weakness.

3. The carrier mold of claim 1, wherein the carrier mold comprises a single integral structure.

4. The carrier mold of claim 1, wherein the carrier mold comprises two or more component pieces.

5. The carrier mold of claim 4, wherein the at least two prongs are component pieces that are separate from the body.

6. The carrier mold of claim 1, wherein the discrete space comprises a maximum arc length.

7. The carrier mold of claim 1, wherein the inner surface comprises a marking means.

8. The carrier mold of claim 7, wherein the marking means spans more than one prong.

9. The carrier mold of claim 1, wherein the distal ends of the at least two prongs include an overhang.

10. The carrier mold of claim 9, wherein the overhang is beveled.

11. A flexible carrier-mold system comprising:
  a. A carrier mold comprising:
    an outer surface, an inner surface, a first end, a second end opposite the first end, a length, a body, a longitudinal axis, and at least two prongs;
    wherein each prong comprises a proximal base, a distal end, and a length;
    wherein the at least two prongs are separated by a discrete space; and
    wherein the inner surface defines an inner cavity for forming shaped tampons, wherein the shaped tampons have a length and comprise varying perimeters along their length, and wherein the inner cavity is structured to define a desired shape of the shaped tampons; and
  b. a shaped tampon comprising varying perimeters along its length;
  wherein the entire shaped tampon fits within the carrier-mold inner cavity;
  wherein the carrier mold first end is completely closed when the at least two prongs are in a closed position; and
  wherein the carrier mold first end is perpendicular to the longitudinal axis when the at least two prongs are in a closed position.

12. The carrier-mold system of claim 11, wherein the carrier mold includes a region of weakness.

13. The carrier-mold system of claim 11, wherein the carrier mold comprises a single integral structure.

14. The carrier-mold system of claim 11, wherein the carrier mold comprises two or more component pieces.

15. The carrier-mold system of claim 14, wherein the at least two prongs are component pieces that are separate from the body.

16. The carrier-mold system of claim 11, wherein the discrete space comprises a maximum arc length.

17. The carrier-mold system of claim 11, wherein the inner surface comprises a marking means.

18. The carrier-mold system of claim 17, wherein the marking means spans more than one prong.

19. The carrier-mold system of claim 11, wherein the distal ends of the at least two prongs include an overhang.

20. The carrier-mold system of claim 19, wherein the overhang is beveled.

* * * * *